(12) United States Patent
Farin (10) Patent No.: US 9,364,335 B2
(45) Date of Patent: Jun. 14, 2016

(54) DEVICE FOR EXPANDABLE SPINAL LAMINOPLASTY

(76) Inventor: Azadeh Farin, Rolling Hills, CA (US)

( * ) Notice: Subject to any disclaimer, the term of this patent is extended or adjusted under 35 U.S.C. 154(b) by 560 days.

(21) Appl. No.: 13/493,978

(22) Filed: Jun. 11, 2012

(65) Prior Publication Data

US 2012/0316647 A1   Dec. 13, 2012

Related U.S. Application Data

(60) Provisional application No. 61/495,786, filed on Jun. 10, 2011.

(51) Int. Cl.
| | |
|---|---|
| *A61F 2/44* | (2006.01) |
| *A61B 17/70* | (2006.01) |
| *A61F 2/30* | (2006.01) |
| *A61F 2/28* | (2006.01) |

(52) U.S. Cl.
CPC ........... *A61F 2/4405* (2013.01); *A61B 17/7071* (2013.01); *A61F 2/30965* (2013.01); *A61F 2/4455* (2013.01); *A61F 2002/2835* (2013.01); *A61F 2002/30471* (2013.01); *A61F 2002/30505* (2013.01); *A61F 2002/30601* (2013.01); *A61F 2002/30637* (2013.01); *A61F 2310/00011* (2013.01); *A61F 2310/00023* (2013.01); *A61F 2310/00161* (2013.01); *A61F 2310/00179* (2013.01); *A61F 2310/00359* (2013.01)

(58) Field of Classification Search
CPC . A61F 2/4405; A61F 2/30965; A61F 2/4455; A61F 2002/2835; A61F 2002/30471; A61F 2002/30505; A61F 2002/30601; A61F 2002/30637; A61F 2310/00011; A61F 2310/00023; A61F 2310/00161; A61F 2310/00179; A61F 2310/00359; A61B 17/7071

USPC ............... 606/86 R, 246, 248, 279, 280–283; 623/17.11, 17.13

See application file for complete search history.

(56) References Cited

U.S. PATENT DOCUMENTS

| | | | |
|---|---|---|---|
| 6,712,852 | B1 | 3/2004 | Chung et al. |
| 6,997,953 | B2 | 2/2006 | Chung et al. |
| 7,264,620 | B2 | 9/2007 | Taylor |
| 8,147,528 | B2 | 4/2012 | Mazzuca et al. |
| 2003/0050641 | A1* | 3/2003 | Mommaerts ................ 606/71 |
| 2005/0273100 | A1* | 12/2005 | Taylor ........................ 606/61 |
| 2006/0089648 | A1* | 4/2006 | Masini ............... A61B 17/1615 606/71 |
| 2008/0009865 | A1 | 1/2008 | Taylor |
| 2010/0057127 | A1 | 3/2010 | McGuire et al. |
| 2010/0152854 | A1* | 6/2010 | Slivka et al. ............ 623/17.12 |
| 2010/0185239 | A1 | 7/2010 | Patel et al. |
| 2010/0241165 | A1 | 9/2010 | Konieczynski et al. |
| 2011/0106168 | A1 | 5/2011 | Bucci et al. |
| 2012/0165942 | A1* | 6/2012 | Khanna ........... A61B 17/7071 623/17.16 |

\* cited by examiner

*Primary Examiner* — Christopher Beccia
*Assistant Examiner* — Diana S Jones
(74) *Attorney, Agent, or Firm* — Steptoe & Johnson LLP (57) ABSTRACT

The invention relates to devices, implants, systems, techniques and methods for addressing certain conditions of the spine, including devices, implants, systems and methods for performing spinal laminoplasty or other expansion of the spinal canal. The devices of the invention are expandable in situ, providing greater versatility for surgeons performing various procedures where expansion of the spinal canal is desired.

2 Claims, 6 Drawing Sheets

DEVICE FOR EXPANDABLE SPINAL LAMINOPLASTY

CROSS-REFERENCE TO RELATED APPLICATIONS

This application makes a claim of priority to U.S. patent application No. 61/495,786, filed Jun. 10, 2011, the contents of which are incorporated herein by reference as though fully set forth.

FIELD OF THE INVENTION

The invention relates to devices, implants, systems, techniques and methods for addressing certain conditions of the spine, including devices, implants, systems, techniques and methods for performing spinal laminoplasty or other expansion of the spinal canal.

BACKGROUND OF THE INVENTION

The spinal cord and nerve roots, or neural elements, pass through the spinal canal, which is composed of vertebrae and ligaments that circumferentially surround the neural elements. When the spinal canal is narrowed, the neural elements can be compressed. The most common condition in which the spinal canal is narrowed is spinal stenosis, which is generally the result of multifactorial degenerative processes usually related to advancing age or repetitive movements of the spine that lead to "wear and tear." In this condition, normal anatomic elements of the spine (discs, ligaments, facets, vertebral endplates) can hypertrophy and degenerate, with a net result of a narrower spinal canal and compression of the neural elements. This compression can cause limb weakness, numbness, pain and gait disturbance.

Spinal decompression can be surgically performed to alleviate the compression of the neural elements with the goal of halting or improving limb weakness, numbness, pain and gait disturbance. One such technique for spinal decompression is spinal laminoplasty, which results in expansion of the spinal canal, thereby alleviating compression of the neural elements. Spinal laminoplasty is performed from the back, or posterior aspect, of the spine. The laminae are the bony elements of the spinal canal posteriorly which are cut during this procedure in order to result in expansion of the spinal canal.

In performing an open door laminoplasty, a drill or other bone cutting device is used to create a full thickness cut through the bony ring surrounding the neural elements at the junction of the laminae and facets on one side; on the other side, a drill or other bone cutting device is usually used to create a groove between the laminae and facets. The unattached laminae from the side with the full thickness cut are then wedged away from the spinal canal and the ligament underneath the laminae is removed. This decompresses the spinal canal by removing a constrictive element and expanding the size of the spinal canal. In a French door laminoplasty, a full thickness cut is made through the midline spinous processes and the midline laminae, enabling wedging open of the spinal canal in the midline as opposed to one side, which is the case with open-door laminoplasty.

An implant is then inserted between laminae and facets or between the two aspects of the spinous process. This implant acts as a connecting bridge between the two ends of cut bone and maintains the expansion of the spinal canal, similar to adding an extra leaf to a dining room table in order to expand it. The implant helps maintain expansion of the spinal canal and thereby decompression of the neural elements because the cross-sectional area of the spinal canal is larger, post-surgery. The implant can be made of cadaver bone, patient's bone, synthetics, metal alloy or a combination thereof.

Many variables in combination determine the best sized implant that should be utilized for laminoplasty, including the patient's anatomy, extent and location of spinal stenosis, and the width of the full thickness cut created during laminoplasty. The width of the cut created during laminoplasty is variable and cannot be predicted ahead of time. In this context, current implants for laminoplasty which are fixed in size have limitations in their versatility because they are not adjustable and can be cumbersome to switch out in favor of a possibly better sized implant if the originally placed implant is the wrong size. Even if the surgeon measures the size of the gap created between two ends of cut bone at the intended site for the laminoplasty implant and either tries to fashion an appropriately sized implant from cadaveric or patient bone or tries to select and modify a prefabricated one from a manufacturer, this can be time consuming and still result in an implant that does not perfectly fit the size and shape of the gap created by the laminoplasty. The gap created when the bone is cut full thickness at the intended implant site is not adjustable once it has been created. A fixed size implant limits the options available for expanding the spinal canal. Its fixed size may be too large or too small and unable to be adjusted to fit the specific anatomic needs of each individual patient. An implant that can be adjusted in situ would allow expansion of the spinal canal at the appropriate length specific to the patient's particular anatomy. None of the currently available implant options are adjustable or customizable in situ in order to appropriately fit the size of the gap whose dimensions itself are unpredictable before surgery and not modifiable once created. This fact limits the range of surgically acceptable configurations that can be achieved through the use of currently available implants. In addition, current implants do not result in any further expansion of the spinal canal should this be required once they are implanted because they are of fixed dimension.

There is therefore a need in the art for an improved laminoplasty device that enables length adjustment while and after it is implanted and also distracts or increases the size of the surgically created gap. An implant that can expand or retract after it has been placed in the laminoplasty gap to meet certain anatomic constraints allows its length to be varied and cancels the need for a custom shaped implant that is time consuming to create and can still be poorly fitted.

BRIEF DESCRIPTION OF THE SEVERAL VIEWS OF THE DRAWING(S)

Exemplary embodiments are illustrated in referenced figures, wherein like numerals refer to like elements. It is intended that the embodiments and figures disclosed herein are to be considered illustrative rather than restrictive.

FIGS. 2A-2D depict the components and operation of a device for use in connection with spinal laminoplasty, in accordance with an embodiment of the present invention.

FIGS. 3A-3D depict the components and operation of a device for use in connection with spinal laminoplasty, in accordance with an embodiment of the present invention.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

The system, devices and methods of the invention are directed to the expansion of the diameter or cross-sectional area of the spinal canal. In certain instances, this may be for the purposes of decompression of neural elements while minimizing destabilization and deformity. The laminoplasty procedure is typically performed in the cervical spine, but those of skill in the art will recognize that it may be performed in other regions of the spine as well. During dissection and exposure, goals may include preservation of certain innate anatomic structures such as ligaments and facets in order to protect the biomechanical integrity of the spine. In general, laminoplasty enables decompression of the neural elements while possibly preserving motion and possibly protecting the spine from instability and kyphotic deformity because the posterior tension band may be preserved to some extent and the facets may be left intact.

The systems and devices of the invention may be configured in many ways, as will be readily apparent to those of skill in the art. Two designs are illustratively depicted herein as laminoplasty devices. They may be principally composed of polyetheretherketone (i.e., PEEK), cadaver bone, or other materials including but not limited to ceramic, carbon fiber, titanium, other metal alloy, expandable/elastic and other materials for the type of application described herein. Both illustrative designs may be lordotic to variable extents (for instance, 6-10 degrees). Both designs may include one or more openings in the devices (e.g., on the top of the devices) that enable a user to insert materials to promote osseous fusion. Both designs may have a component that articulates with the lateral mass or facet; a centerpiece component that expands the diameter of the spinal canal; and a component that articulates with the lamina or spinous process. Alternatively the device may articulate with the spinous process only or other component of the spinal canal. The components that articulate with bone may be coated with a material that enhances osseous fusion locally at the point of contact between implant and bone, with or without intended fusion across vertebral segments depending on whether or not motion preservation is a surgical objective. These materials may include but are not limited to hydroxyappetite or bone morphogenetic protein in the appropriate amount to enhance osseous fusion of the laminoplasty implant to bone.

Figure 1:
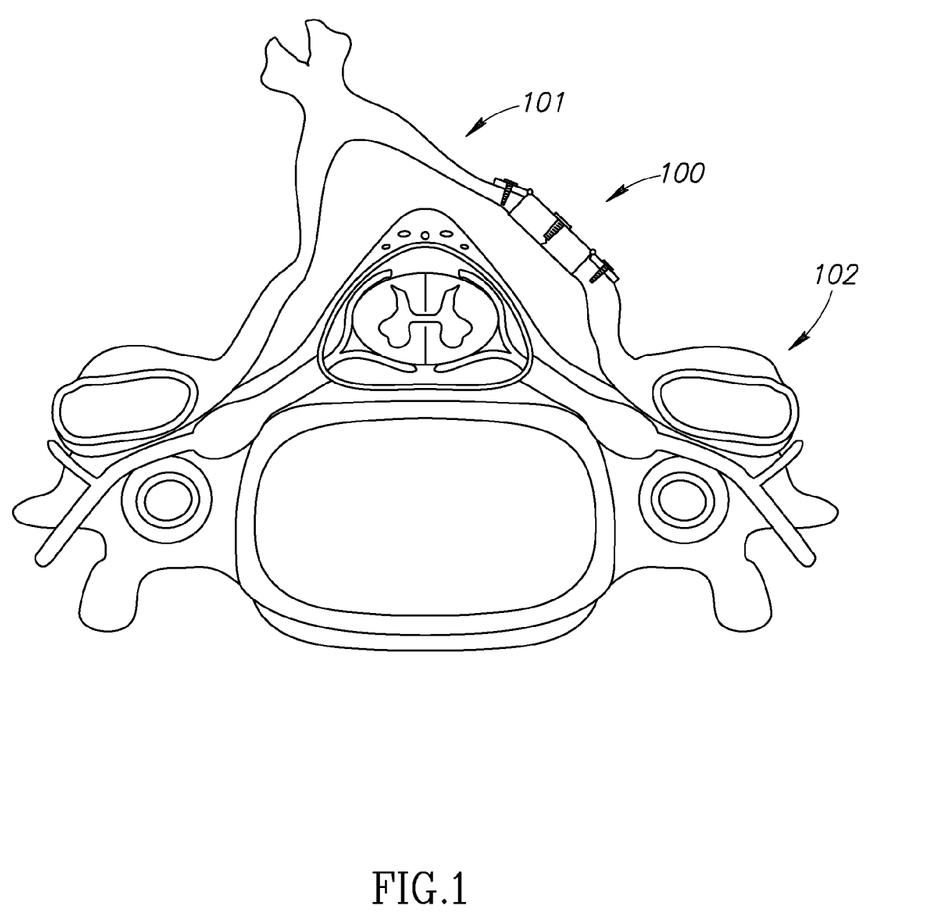
FIG. 1 depicts a cross-sectional view of a device of the invention deployed between a lamina and a lateral mass, in accordance with an embodiment of the present invention.
Figure 2A:
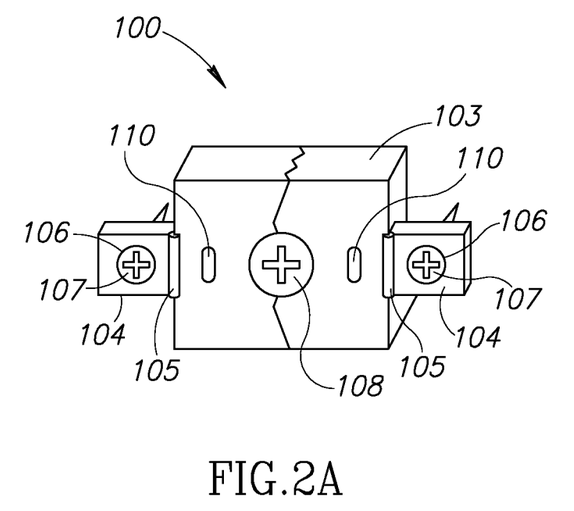
FIGS. 2A and 2B depict top views of the device in its initial and expanded states, respectively.
Figure 2B:
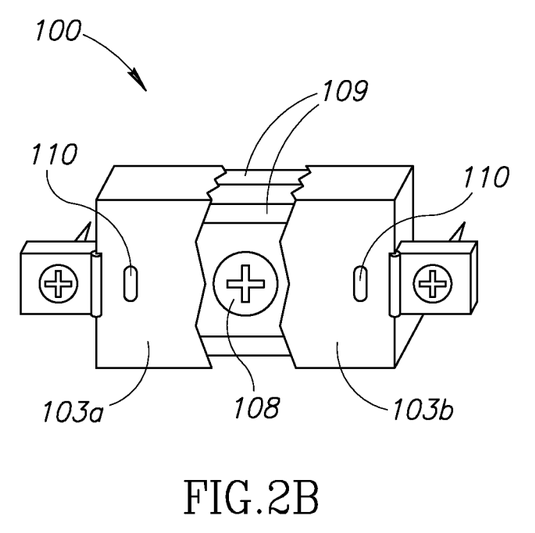
Figure 2C:
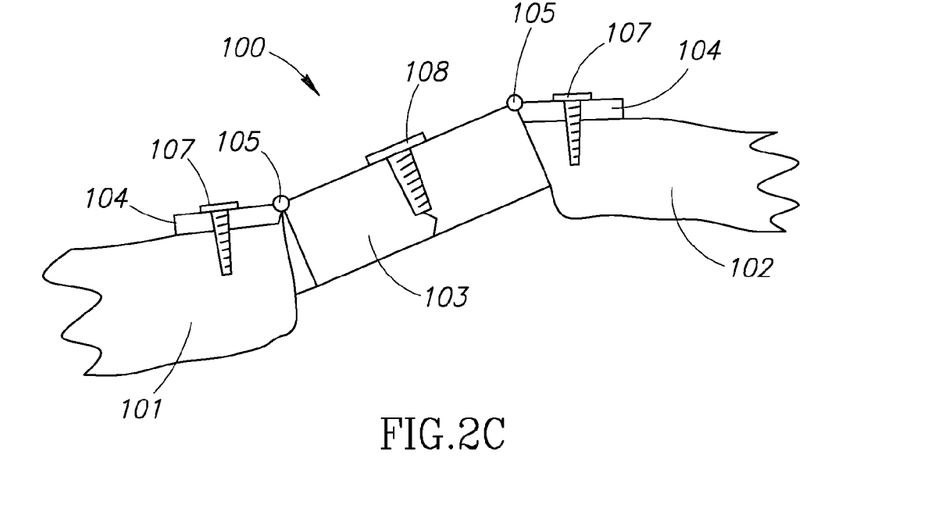
FIGS. 2C and 2D depict side views of the device in its initial and expanded states, respectively.
Figure 2D:
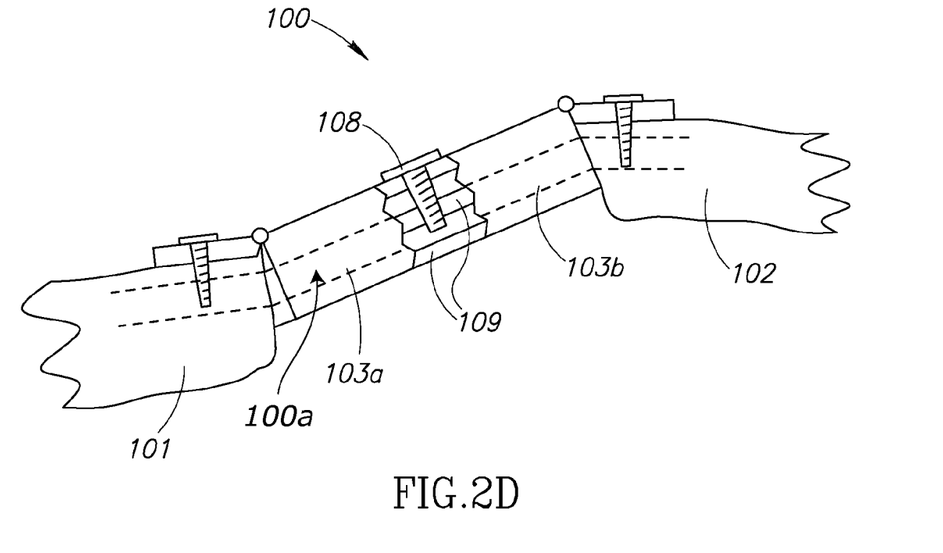
Figure 3A:
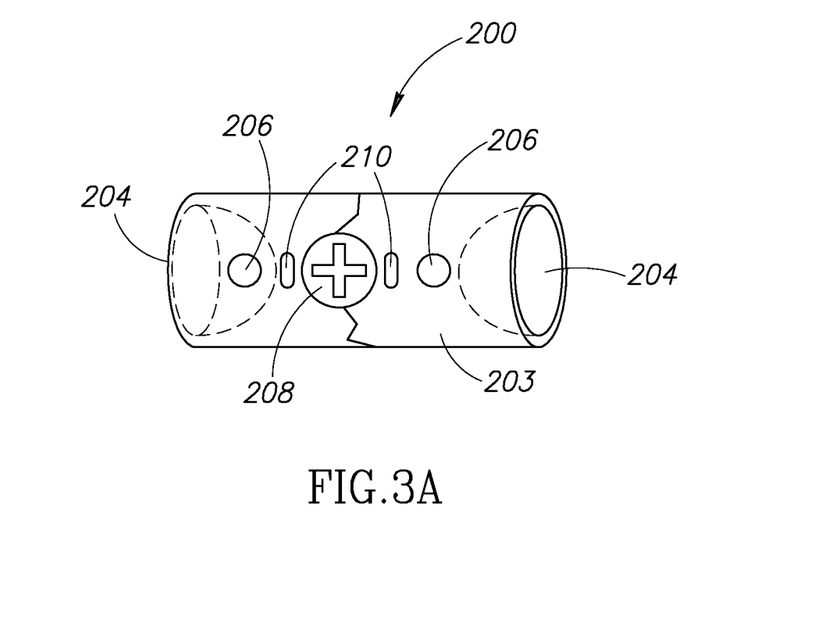
FIGS. 3A and 3B depict top views of the device in its initial and expanded states, respectively.
Figure 3B:
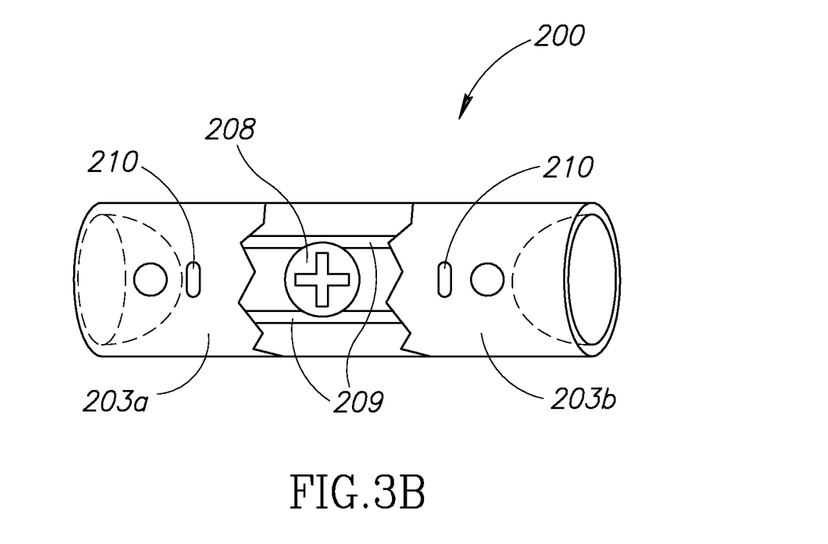
Figure 3C:
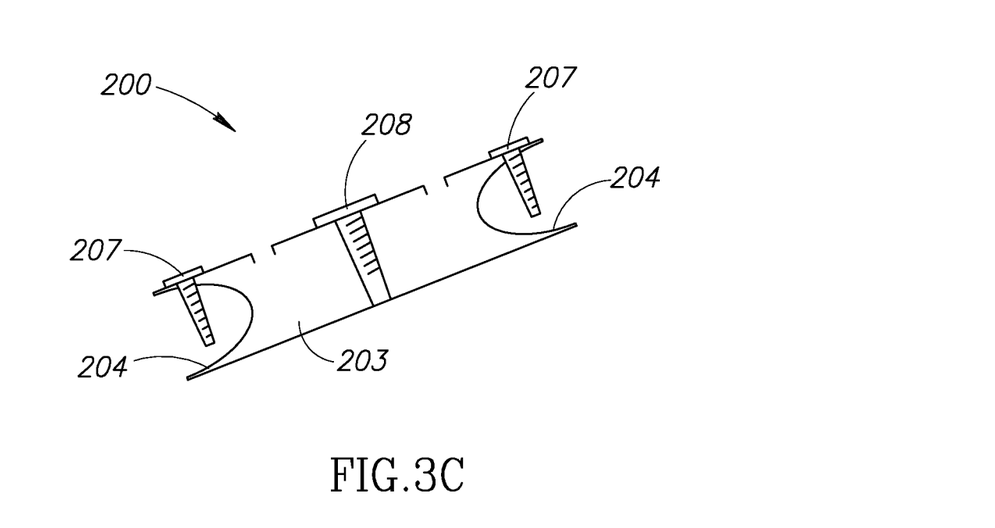
FIGS. 3C and 3D depict side views of the device in its initial and expanded states, respectively.
Figure 3D:
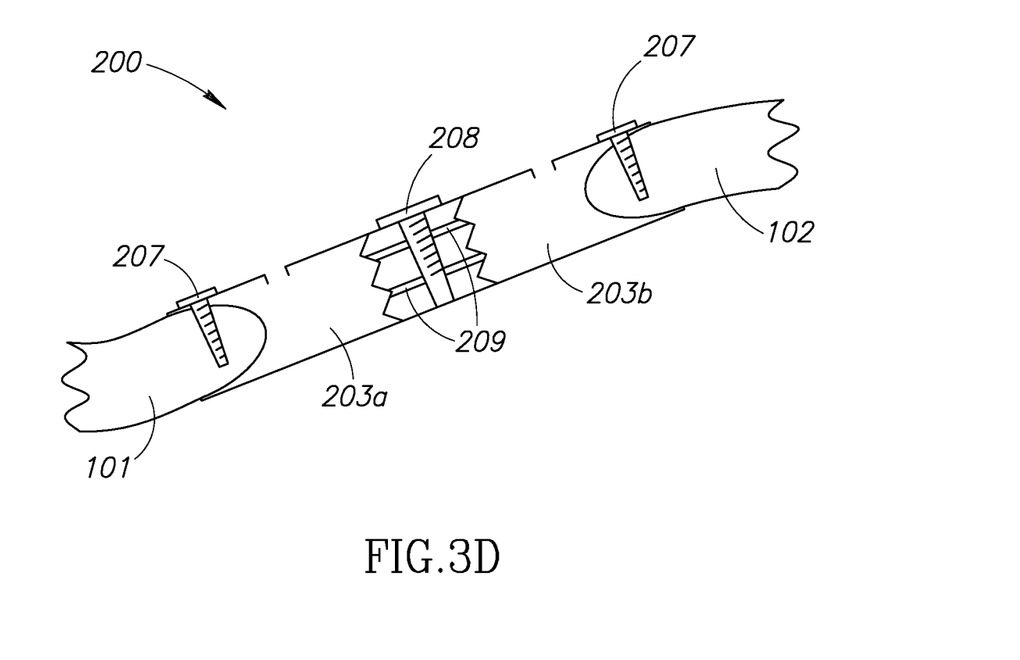

An embodiment of the invention is illustrated in FIG. 1, where the inventive device 100 is shown in situ, deployed between a lamina 101 and a lateral mass 102, in accordance with an embodiment of the present invention. The device may also be deployed elsewhere to expand the spinal canal, including but not limited to between two halves of the spinous process that has been split, as with a French door laminoplasty (not shown).

As illustrated in FIG. 2, the device 100 may have a centerpiece 103 in mechanical communication with each of two attachment components 104 by way of two hinges 105 or other element that allows some rotation or flexibility of the attachment components in order to best fit the bone to which the attachment components are being attached and to enable the implant to best occupy the groove that has been created. The hinges 105 may be composed of metal, plastic or other material as will be readily appreciated by those of skill in the art. In alternate embodiments, the hinges may be substituted with other adjustable elements residing between the centerpiece and attachment components. This configuration enables customization of the device 100 (such as the angle between each of the attachment components 104 and the centerpiece 103) to fit the anatomic requirements of the patient at each particular level with little time consumption. The device 100 may be prefabricated with a predetermined bend angle between the centerpiece 103 and each attachment component 104 (e.g., in the hinges 105), although it may nonetheless be configured so as to allow further manipulation by the surgeon if necessary so that the device 100 resides in a desired location and at a desired configuration within the laminoplasty groove.

Each of the attachment components 104 may include a hole 106 configured for an elongated element 107 to traverse. The elongated element 107 may be of variable dimension, and may be used to secure the device 100 to the lateral element, facet, spinous process or other component of the spine. In an embodiment, the elongated element is a screw of about 5 mm to about 10 mm in length (e.g., an 8 mm screw), nail, staple or other fixation mechanism. If a screw or nail or similar component is used for this purpose, for example, trajectory may be angled; for instance, about 25°, 30° or 35° superiorly and laterally. Each attachment component 104 may have a truncated or otherwise complementary-shaped footpiece that contacts the medial aspect of the lateral mass, facet, spinous process or other component of the bony spine, or an overhanging or underhanging element that resides above, under or adjacent to the lateral element, facet, spinous process or other component of the bony spine 101 or 102.

The device 100 includes an actuator 108 in the centerpiece; whereby rotating or 5 otherwise deploying it actuates medial-lateral or other expansion of the centerpiece and optionally the entire laminoplasty implant along one or more expansion rails 109. In the device 100 illustratively depicted in FIG. 2, the actuator 108 is a screw that is rotated (i.e., counterclockwise or clockwise, depending upon the configuration of the device 100), but in alternate embodiments, the actuator may be a center lever that is manipulated from one direction to the other (not shown). Upon actuation, a first portion of the centerpiece 103a distracts away from a second portion of the centerpiece 103b. When the desired extent of expansion has been achieved, a fixation mechanism (such as an inner screw, nail, lever, dial or other stabilizing element that may reside within or adjacent to the actuator 108) may then be locked to secure the final expansion size and not allow further change in size configuration of the implant unless the device 100 is unlocked first. In an embodiment, after expansion of the device 100 has been completed, the hollow component of the centerpiece 103 may be filled with material promoting osseous segmental or intersegmental fusion such as demineralized bone matrix or other material, which can be inserted through orifices 110. As the fusion-enhancing material fills the centerpiece, it may then continue to move through one or more hollow channels 100a within the device 100 to eventually make contact with patient's bone at both ends of the device 100. The material will therefore be in contact with the patient's own bone through the entire laminoplasty implant, and fusion will be prone to occur from one end of the cut bone through the implant through to the other end of cut bone.

As illustrated in FIG. 3, in another embodiment of the invention, a device 200 may have a centerpiece 203 with one or both of its two ends 204 configured with a generally concave or other complimentary configuration so that there is fit-press articulation with the lateral mass, facet, spinous process, lamina or other spine component 101 or 102 with which it is configured to interact upon use. The device may be prefabricated in a variety of configurations as will be readily appreciated by those of skill in the art, such that, upon placement in situ, the device mechanically and morphologically complements the anatomy with which it interacts. This may be both in terms of the configuration of the two ends (e.g., the precise contour(s) of the generally concave surfaces 204) and/or the overall device design and shape (e.g., the angle relative to one another in which the two ends move upon device actuation; FIG. 3B illustrates a 180° expansion angle, but other angles may be used in connection with alternate embodiments of the invention, such as, but not limited to, about 90°, 120°, 150°, 160° or 170°.

Each of the two ends 204 may include a hole 206 configured for an elongated element 207 to traverse. The elongated element 207 may be of variable dimension, and may be used to secure the device 200 to the lateral element, facet, spinous process or other component of the spine 101 or 102. In an embodiment, the elongated element is a screw of about 5 mm to about 10 mm in length (e.g., an 8 mm screw), nail, staple or other fixation mechanism. If a screw or nail or similar component is used for this purpose, for example, trajectory may be angled; for instance, about 25°, 30° or 35° superiorly and/or laterally.

The device 200 includes an actuator 208 in the centerpiece 203; whereby rotating or otherwise deploying it actuates medial-lateral or other expansion of the centerpiece 203 along one or more expansion rails 209. In the device 200 illustratively depicted in FIG. 3, the actuator 208 is a screw that is rotated (i.e., counterclockwise or clockwise, depending upon the configuration of the device 200), but in alternate embodiments, the actuator may be a center lever that is manipulated from one direction to the other (not shown). Upon actuation, a first portion of the centerpiece 203a distracts away from a second portion of the centerpiece 203b. When the desired extent of expansion has been achieved, a fixation mechanism (such as an inner screw, nail, lever, dial or other stabilizing element that may reside within or adjacent to the actuator 208) may then be locked to secure the final expansion size and not allow further change in size configuration of the implant unless the device 200 is unlocked first. In an embodiment, after expansion of the device 200 has been completed, the hollow component of the centerpiece 203 may be filled with material promoting osseous segmental or intersegmental fusion such as demineralized bone matrix or other material, which can be inserted through orifices 210, and which will eventually contact patient's own bone through the attachment component as described previously.

Figure 4A:
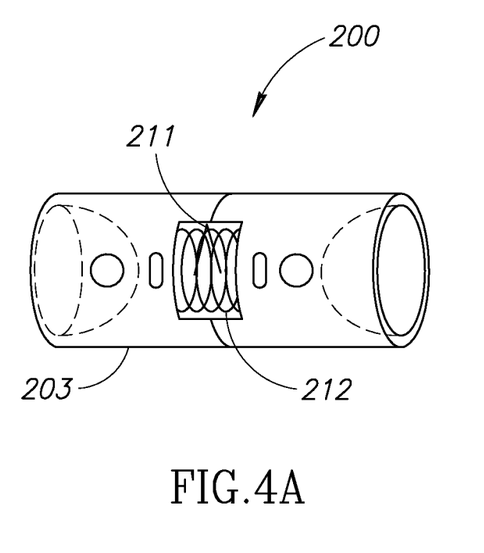
FIGS. 4A-4B depict the components and operation of the device described in FIGS. 3A-3D, but wherein the actuator has been replaced with a spring-loaded coil and clip arrangement, in accordance with an embodiment of the present invention.
Figure 4B:
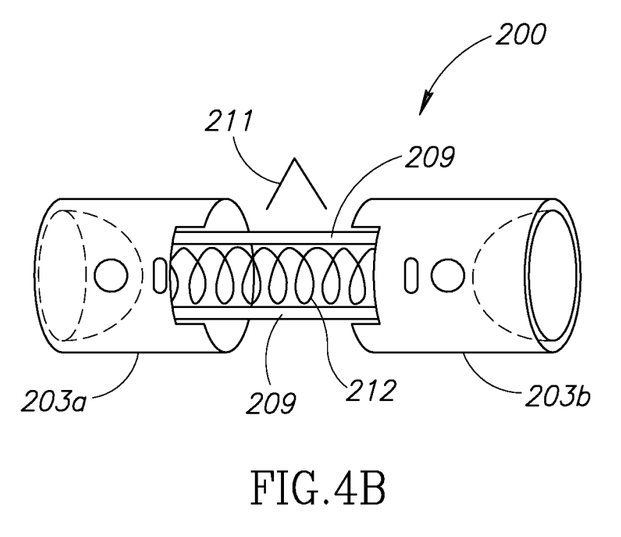

FIG. 4 illustrates an alternate embodiment of the device 200, wherein the actuator is replaced by a spring-loaded coil 212 that connects to both elements 203a, 203b of the centerpiece 203. Initially, a clip 211 holds the coil 212 in a compressed position. When the device 200 is properly positioned, the clip 211 is removed, thereby releasing the coil 212. The two elements 203a, 203b of the centerpiece 203 then expand to close the laminoplasty gap or up to a point limited by the edges of bone on either side—either lamina and lateral mass or two halves of spinous process. The tension in the coil 212 is predetermined such that the two elements 303a, 303b of the centerpiece 303 move away from each other until they are tightly opposed with bone and offer some resistance to the cut bone edge in order to maintain the expansion of the spinal canal. Alternatively, a larger laminoplasty gap can be created by pushing the lamina away at the cut edge; the spring-loaded coil enables the centerpiece to expand appropriately to the extent necessary to occupy a variety of gap sizes.

In an embodiment, the invention further includes a method of expanding the diameter and cross-sectional area of the spinal canal by providing a device as herein described, inserting the device between a lamina and a lateral mass, or between two ends of a split spinous process, or elsewhere within the spine, and expanding the device. The method may include affixing the device to the lamina and/or lateral mass or other spinal elements with a mechanical element such as a screw or other fixation device such as nail, staple, or other component.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Various embodiments of the invention can specifically include or exclude any of these variations or elements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

I claim:

1. A medical device, comprising:
   a centerpiece comprising a first portion and a second portion;
   an actuator or a spring-loaded coil and clip, to control expansion of the centerpiece by the first portion and the second portion moving away from one another upon actuation of the actuator or release of the coil, respectively;
   one or more expansion rails each in mechanical communication with at least one of the first portion and the second portion of the centerpiece, wherein upon actuation of the actuator or release of the coil the expansion rails force the first portion and the second portion to move away from one another;
   two elements, each configured to independently interact with two components of the bony spine, each independently attached to the first portion and second portion of the centerpiece, respectively, by each of two flexible members that allow angular movement but do not allow translational movement between the two elements and first and second portions of the centerpiece; and
   wherein the centerpiece comprises at least one orifice adapted to receive an amount of material promoting osseous intrasegmental fusion following expansion of the centerpiece.

2. A medical device, comprising:
   a centerpiece comprising a first portion and a second portion;
   an actuator or a spring-loaded coil and clip, to control expansion of the centerpiece by the first portion and the second portion moving away from one another upon actuation of the actuator or release of the coil, respectively;
   one or more expansion rails each in mechanical communication with at least one of the first portion and the second portion of the centerpiece, wherein upon actuation of the actuator or release of the coil the expansion rails force the first portion and the second portion to move away from one another;
   a fixation mechanism in mechanical communication with either the actuator or the spring-loaded coil, and in mechanical communication with the expansion rails or the first portion and the second portion of the centerpiece, to secure a final expansion configuration of the medical device;
   two elements, each configured to independently interact with two components of the bony spine, each independently attached to the first portion and second portion of the centerpiece, respectively, by each of two flexible members that allow angular movement but do not allow translational movement between the two elements and first and second portions of the centerpiece; and
   wherein the centerpiece comprises at least one orifice adapted to receive an amount of material promoting osseous intrasegmental fusion following expansion of the centerpiece.

* * * * *